United States Patent
Kieser et al.

(10) Patent No.: US 10,888,430 B2
(45) Date of Patent: Jan. 12, 2021

(54) EXPANDABLE/VARIABLE LORDOTIC ANGLE VERTEBRAL IMPLANT AND READING SYSTEM THEREFOR

(71) Applicant: NVision Biomedical Technologies, LLC, San Antonio, TX (US)

(72) Inventors: Brian Kieser, San Antonio, TX (US); Thomas Zink, San Antonio, TX (US); Nicholas Cordaro, Vista, CA (US); Frank Kuwamura, III, San Antonio, TX (US)

(*) Notice: Subject to any disclaimer, the term of this patent is extended or adjusted under 35 U.S.C. 154(b) by 0 days.

(21) Appl. No.: 16/013,035

(22) Filed: Jun. 20, 2018

(65) Prior Publication Data

US 2018/0368984 A1 Dec. 27, 2018

Related U.S. Application Data

(60) Provisional application No. 62/523,090, filed on Jun. 21, 2017.

(51) Int. Cl.
| | |
|---|---|
| *A61F 2/44* | (2006.01) |
| *A61B 90/98* | (2016.01) |
| A61B 90/94 | (2016.01) |
| A61B 5/055 | (2006.01) |
| A61B 8/08 | (2006.01) |

(Continued)

(52) U.S. Cl.
CPC .............. *A61F 2/442* (2013.01); *A61B 90/98* (2016.02); *A61F 2/4455* (2013.01); *A61F 2/4465* (2013.01); *A61B 5/055* (2013.01); *A61B 6/12* (2013.01); *A61B 8/0833* (2013.01); *A61B 90/90* (2016.02); *A61B 90/94* (2016.02); *A61F 2002/3071* (2013.01); *A61F 2002/30266* (2013.01); *A61F 2002/30387* (2013.01); *A61F 2002/30593* (2013.01); *A61F 2002/30733* (2013.01)

(58) Field of Classification Search
CPC .. A61F 2/4455–447; A61F 2002/3071–30714; A61F 2002/30716–30718
See application file for complete search history.

(56) References Cited

U.S. PATENT DOCUMENTS

| | | | |
|---|---|---|---|
| 6,102,950 A * | 8/2000 | Vaccaro ................ | A61F 2/4611 606/247 |
| 6,179,874 B1 * | 1/2001 | Cauthen ............. | A61B 17/1671 623/17.14 |

(Continued)

*Primary Examiner* — Ellen C Hammond
(74) *Attorney, Agent, or Firm* — Brennan, Manna & Diamond, LLC (57) ABSTRACT

A structurally encoded implant comprising a pair of endplates movably secured at the posterior end via a slip joint and a wedge component. The wedge component is inserted between the pair of endplates to increase implant height and change the lordotic angle. The pair of endplates may be manufactured together as one integral component using additive manufacturing techniques. During this additive manufacturing process, water-soluble support material may be positioned around the slip joint. Once the pair of endplates is formed, the support material may be dissolved away, allowing the pair of endplates to move independently from one another, but to still remain movably attached via the slip joint, such that the pair of endplates allow for height expansion and lordotic angle change.

20 Claims, 4 Drawing Sheets

(51) Int. Cl.
   *A61B 6/12* (2006.01)
   *A61F 2/30* (2006.01)
   *A61B 90/90* (2016.01)

(56) References Cited

U.S. PATENT DOCUMENTS

| | | | |
|---|---|---|---|
| 6,685,742 B1* | 2/2004 | Jackson | A61F 2/447 623/17.11 |
| 7,887,588 B2* | 2/2011 | Rapp | A61F 2/4455 623/17.11 |
| 8,267,999 B2* | 9/2012 | Beaurain | A61F 2/442 623/17.11 |
| 8,454,700 B2* | 6/2013 | Lemoine | A61F 2/4465 606/249 |
| 9,101,321 B1* | 8/2015 | Kieser | A61B 17/7004 |
| 9,414,932 B2* | 8/2016 | Errico | A61F 2/442 |
| 9,445,919 B2* | 9/2016 | Palmatier | A61F 2/447 |
| 9,815,118 B1* | 11/2017 | Schmitt | B33Y 30/00 |
| 9,839,527 B2* | 12/2017 | Robinson | A61F 2/447 |
| 10,105,235 B2* | 10/2018 | Ledet | A61F 2/44 |
| 10,111,758 B2* | 10/2018 | Robinson | A61F 2/447 |
| 2002/0068976 A1* | 6/2002 | Jackson | A61F 2/4455 623/17.15 |
| 2008/0300634 A1* | 12/2008 | Gray | A61B 17/7059 606/280 |
| 2009/0148813 A1* | 6/2009 | Sun | A61C 13/0001 433/201.1 |
| 2010/0191336 A1* | 7/2010 | Greenhalgh | A61F 2/4455 623/17.16 |
| 2010/0286777 A1* | 11/2010 | Errico | A61F 2/442 623/17.11 |
| 2010/0324686 A1* | 12/2010 | Gerner | A61F 2/44 623/17.16 |
| 2011/0153020 A1* | 6/2011 | Abdelgany | A61F 2/4465 623/17.16 |
| 2011/0288644 A1* | 11/2011 | Gray | A61F 2/4465 623/17.11 |
| 2012/0226319 A1* | 9/2012 | Armstrong | A61B 17/7059 606/279 |
| 2012/0271422 A1* | 10/2012 | Miller | A61F 2/447 623/17.16 |
| 2013/0053680 A1* | 2/2013 | Frey | A61B 6/12 600/411 |
| 2013/0103154 A1* | 4/2013 | Trieu | A61F 2/442 623/17.16 |
| 2014/0094917 A1* | 4/2014 | Salerni | A61F 2/447 623/17.16 |
| 2014/0114420 A1* | 4/2014 | Robinson | A61F 2/447 623/17.16 |
| 2014/0148904 A1* | 5/2014 | Robinson | A61F 2/447 623/17.16 |
| 2014/0194990 A1* | 7/2014 | He | A61F 2/4465 623/17.14 |
| 2015/0148908 A1* | 5/2015 | Marino | A61F 2/4455 623/17.16 |
| 2015/0351925 A1* | 12/2015 | Emerick | A61F 2/447 623/17.16 |
| 2016/0042261 A1* | 2/2016 | Kieser | G06K 19/06046 235/489 |
| 2017/0095335 A1* | 4/2017 | Kieser | A61F 2/30 |
| 2017/0216036 A1* | 8/2017 | Cordaro | A61F 2/4455 |
| 2017/0231778 A1* | 8/2017 | Overes | A61F 2/4465 623/17.16 |
| 2017/0333199 A1* | 11/2017 | Sharifi-Mehr | A61F 2/447 |
| 2017/0333200 A1* | 11/2017 | Arnin | A61F 2/4425 |
| 2017/0367843 A1* | 12/2017 | Eisen | A61F 2/30734 |
| 2017/0367845 A1* | 12/2017 | Eisen | A61F 2/4425 |
| 2018/0071111 A1* | 3/2018 | Sharifi-Mehr | A61F 2/441 |
| 2018/0104066 A1* | 4/2018 | Bae | A61F 2/4455 |
| 2018/0368992 A1* | 12/2018 | Zink | A61F 2/4465 |
| 2019/0110901 A1* | 4/2019 | Suddaby | A61F 2/4455 |
| 2019/0167441 A1* | 6/2019 | Suddaby | A61F 2/4425 |
| 2019/0231551 A1* | 8/2019 | Freedman | A61B 17/1728 |

\* cited by examiner

EXPANDABLE/VARIABLE LORDOTIC ANGLE VERTEBRAL IMPLANT AND READING SYSTEM THEREFOR

CROSS-REFERENCE TO RELATED APPLICATION

This application incorporates by reference all of the following: (i) U.S. Provisional Patent Application No. 61/938,475, filed Feb. 11, 2014; (ii) U.S. patent application Ser. Nos. 14/302,133, 14/302,171 (now U.S. Pat. No. 9,101,321) and Ser. No. 14/302,197, all filed Jun. 11, 2014; (iii) U.S. patent application Ser. No. 14/456,665, filed Aug. 11, 2014; (iv) U.S. Provisional Patent Application No. 62/035,875, filed Aug. 11, 2014; (v) U.S. patent application Ser. No. 14/823,234, filed Aug. 11, 2015 (now U.S. Pat. No. 9,424,503); (vi) U.S. patent application Ser. No. 14/822,613, filed Aug. 10, 2015 (now U.S. Pat. No. 9,414,891); (vi) U.S. Provisional Patent Application No. 62/204,233, filed Aug. 12, 2015; (vii) U.S. patent application Ser. No. 15/235,914, filed Aug. 12, 2016; (vii) U.S. Provisional Patent Application No. 62/419,341, filed Nov. 8, 2016; (viii) U.S. patent application Ser. No. 15/806,482, filed Nov. 8, 2017; (ix) U.S. patent application Ser. No. 15/805,317, filed Nov. 7, 2017; and (x) Provisional Patent Application Ser. No. 62/523,090 filed on Jun. 21, 2017.

This application claims priority from U.S. Provisional Patent Application Ser. No. 62/523,090 filed on Jun. 21, 2017.

FIELD OF THE INVENTION

The present invention relates generally a vertebral implant, and more particularly to a preferably additively manufactured implant with variable lordotic angle and that is expandable in vivo, as well as a reading system therefor, and methods of identifying and encoding implants, and systems for identifying and encoding implanted devices with structurally encoded data.

BACKGROUND

A number of medical conditions such as compression of spinal cord nerve roots, degenerative disc disease, tumor, and trauma can cause severe back pain. Intervertebral fusion is one surgical method of alleviating back pain. In an intervertebral fusion procedure, two adjacent vertebral bodies are fused together by removing the affected intervertebral disc and inserting an implant that would allow for bone to grow between the two vertebral bodies to bridge the gap left by the disc removal. Another surgical method of relieving back pain is by corpectomy. In a corpectomy procedure, a diseased or damaged vertebral body along with the adjoining intervertebral discs are removed and replaced by a spinal implant that would allow for bone to grow between the closest two vertebral bodies to bridge the gap left by the spinal tissue removal.

A number of different implant materials and implant designs have been used for interbody fusion and for vertebral body replacement with varying success. Current implant materials used include metals, radiolucent materials including plastics, elastic and polymeric materials, ceramic, and allografts. Current implant designs vary from threaded cylindrical implants to rectangular cages with teeth-like protrusions.

Interbody vertebral spacers are also known that are inserted between the vertebrae bodies to replace a collapsed, degenerated, or unstable disc. However, these prior art spacers were typically of a predetermined thickness and thus it was difficult to size the thickness of the spacer in order to achieve the desired amount of distraction between the adjacent vertebra bodies.

Furthermore, certain adjustable height interbody fusion devices are known, such as described in U.S. Pat. No. 6,080,193 that vary the distance between the portions of the spacer that engage the endplates of the adjacent vertebrae. However, these adjustable fusion devices rely on cams and other complicated mechanisms that are difficult to adjust after implantation.

Additionally, it would be advantageous to have an implant matching the existing anatomy so that the two surfaces of the implant would better conform to and better fit the shape of the disc space so that load sharing occurs over the whole implant. Otherwise, an implant having parallel upper and lower surfaces used in a disc space having, for example, 8 degrees of in situ lordosis, would result in only part of the implant contacting its respective vertebrae bodies and therefore lessening the corrective support applied to the spine and thus predisposing the implant to subsidence. In this context, subsidence refers to an increased tendency of the implant, over time, to telescope, settle or project into the adjacent vertebrae bodies with loss of disc space height back to preoperative levels. Thus, it would be desirable to use a variable height implant that could reconstruct any disc space anatomy or morphology surgically encountered including, without limitation, lordotic conditions.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

In one preferred embodiment of the present invention, the implant device comprises a pair of endplates that move independently from one another and a wedge component. The wedge component is inserted between the pair of endplates to increase implant height and to change the lordotic angle. Each of said pair of endplates preferably comprises an outboard surface, an inboard surface, opposing lateral sides, opposing anterior and posterior portions, and a continuous opening therein extending from the outboard surface to the inboard surface to, among other things, promote bone growth. The wedge component also preferably comprises a top surface, a bottom surface, opposing lateral sides, opposing anterior and posterior portions, a bar lock positioned on said anterior portion, and a continuous opening therein extending from the top surface of the wedge to the bottom surface of the wedge to, among other things, promote bone growth. Further, the wedge component comprises structurally encoded data, for example, in the form of a vertical rod.

In a preferred embodiment of the present invention, the pair of endplates is movably secured to one other at the posterior end via a slip joint. Further, the pair of endplates may be manufactured (or grown) together as one integral component using additive manufacturing techniques. During this additive manufacturing process, water-soluble support material may be positioned around the slip joint. Once the pair of endplates is formed, the support material may be dissolved away, allowing the pair of endplates to move independently from one another, but to still remain movably attached via the slip joint, such that the pair of endplates allow for height expansion and lordotic angle change. Specifically, the wedge component is inserted between the pair of endplates at their anterior ends and pushes apart the pair of endplates at their anterior ends causing their posterior ends to rise.

In a further preferred embodiment of the present invention, the wedge component may also comprise notches or other radiopaque inclusions (e.g., on its lateral sides) that interrupt an otherwise uniform surface, that can be coded to match the encoded markers that may be pressed into the implant device in accordance with inventions disclosed in the incorporated references. Such encoding may be accomplished for instance through the use of eclipsing patterns of marks or notches in other planes within the wedge component (as opposed to just the surface), to reveal a pattern upon elucidation through reading illumination or through illumination-aided visual inspection or optical inspection, as described herein.

The displayed pattern may be used and stored as a unique symbol such as may be done in a fashion similar to bar codes, or other direct correspondence to a file of information such as through pattern recognition. The encoded pattern may further be associated with a database containing a plurality of records associated with a plurality of implantable devices and a user interface comprising means for displaying information associated with the indicia based on the plurality of records. The structurally encoded pattern may in turn be related to a unique numerical identifier corresponding to the associated manufacturer, serial number, installation data, patient, surgeon, or surgical procedure information that may be located in an external healthcare facility or other database.

The reading illumination may be that of any appropriate imaging modality such as those selected from the group consisting of visible light, UV light, x-ray, fluoroscopy, computed tomography, electromagnetic radiation, ultrasound, magnetic resonance imaging, positron emission tomography and neutron imaging, depending upon the nature and thickness of the implant body and the constituent adjacent first and second encoded regions and constituent series of shaped inclusions.

The implants of the present invention and the methods relating to same may further incorporate the structurally encoded pin and the applicable methods relating to the same as described in U.S. patent application Ser. No. 15/806,482, filed on Nov. 8, 2017 and entitled Elongate Implant Containing a Structurally Encoded Pin, Carrier and Reading System Therefor. Accordingly, the implants of the present invention may be directly encoded or further comprise a structurally encoded component such as a pin. Further embodiments may also include the use of embedded chips, etc. in the implant.

Accordingly, implants of the present invention may have encoded therein some information through the use of the encoded inclusion patterns of the present invention, while other information may be encoded through use of the structurally encoded pins described in the referenced application. Likewise, by combining aspects of both inventions, one can use the two (or more) methods together for similar information (either for redundancy or using different methods for reading the information), different information, or some combination of the same or different information, as well as further through the use of embedded chips, etc. for other information within such an encoding scheme.

The implant of the present invention may be read by any illuminating means, such as x-rays and the like, so as to permit all of the encoded implants to be viewed (and decoded) to permit inventory to be tracked and managed in the same manner as the subject implants may be tracked and managed both before and after introduction into the body.

The present invention may also be applied to other industries, thereby allowing the operator to track anything in any industry with an eclipsing encoded region as described herein and a source of reading illumination, such as x-rays or the like. For example, it will be appreciated that the present invention may also be applied to other fields for the inventory management of articles in any industry, such as in the case of articles that may include parts used in manufacturing, such as in the case of automobiles, firearms, jewelry, etc., as well as parts therefor.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

DETAILED DESCRIPTION

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

Generally stated, the present invention discloses an implant comprising a pair of endplates movably secured at the posterior end via a slip joint and a wedge component. More specifically, the wedge component is inserted between the pair of endplates to increase implant height and change lordotic angle. The pair of endplates may be manufactured together as one integral component using additive manufacturing techniques, and a water-soluble support material may be positioned around the slip joint. Once the pair of endplates is formed, the support material may be dissolved away, thereby allowing the pair of endplates to move independently from one another but to still remain movably attached via the slip joint, such that the pair of endplates allow for height expansion and lordotic angle change.

Figure 1:
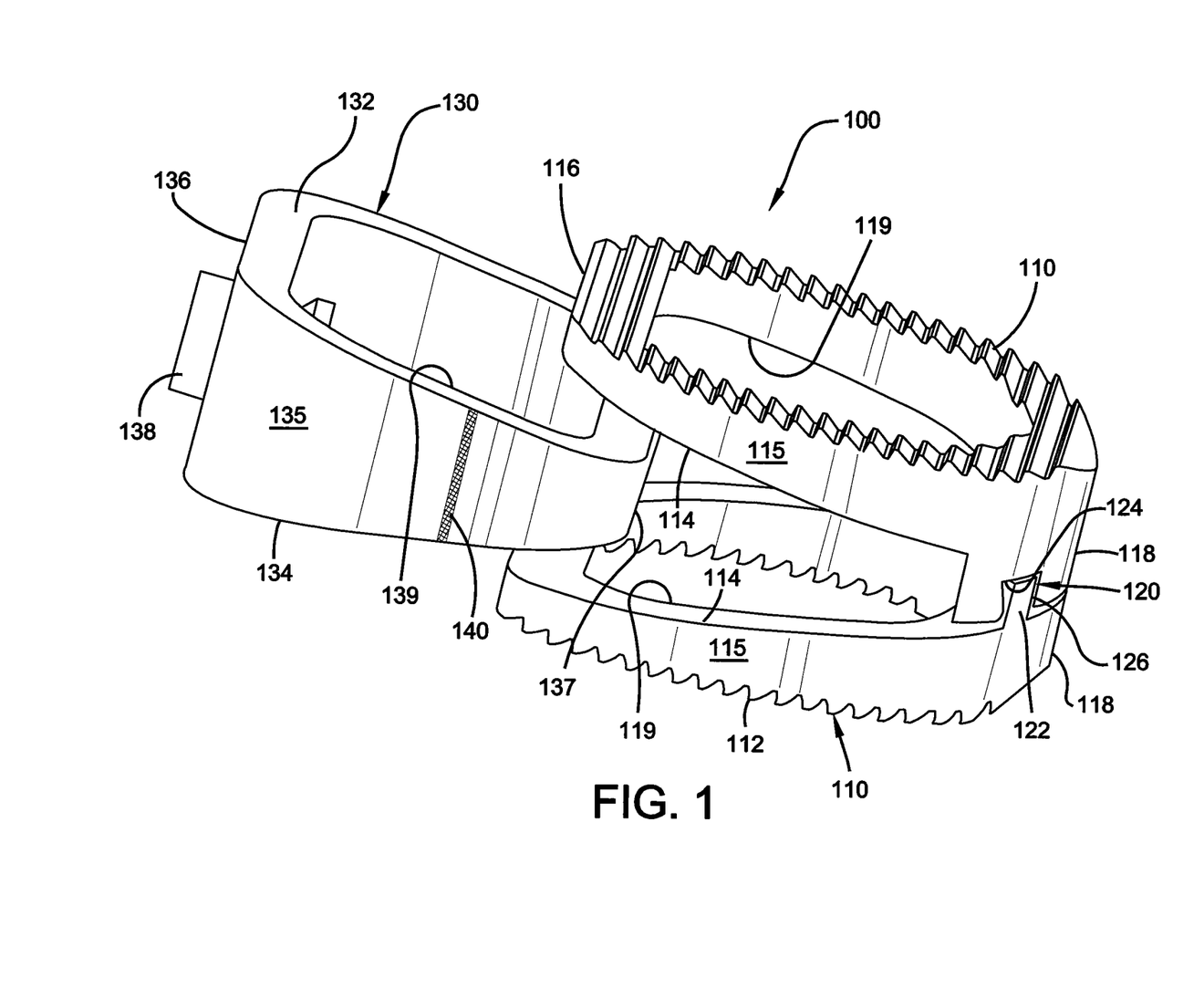
FIG. 1 illustrates a side perspective and exploded view of one embodiment of the vertebral implant of the present invention in accordance with the disclosed architecture.

Referring initially to the drawings, FIG. 1 illustrates a side perspective and exploded view of one embodiment of a vertebral implant 100 of the present invention. Implant 100 is preferably comprised of a pair of endplates 110 that move independently from one another and a wedge component 130. Wedge component 130 is inserted between the pair of endplates 110 to increase the overall height of implant 100 and to change lordotic angle. More specifically, wedge component 130 is inserted between the pair of endplates 110 at their anterior ends and pushes apart the pair of endplates 110 at their anterior ends causing said anterior ends to rise, as explained more fully below.

As best shown in FIGS. 1, 2 and 4A and 4B, each of endplates 110 is further comprised of an outboard surface 112, an inboard surface 114, opposing lateral sides 115, opposing anterior 116 and posterior portions 118, and a substantially hollow center or continuous opening 119 therein extending from outboard surface 112 to inboard surface 114 to, among other things, promote bone growth. As best shown in FIGS. 1, 2 and 4A and 4B, outboard surfaces 112 are preferably roughened or ridged so as to better grip the adjacent vertebra once installed in a patient. More specifically, the roughened outboard surface 112 provides anti-migration features for implant 100 once inserted into the body, and also provides osteo-integration allowing bone to grow within the outboard surface 112 to further secure implant 100 within the body.

Figure 2:
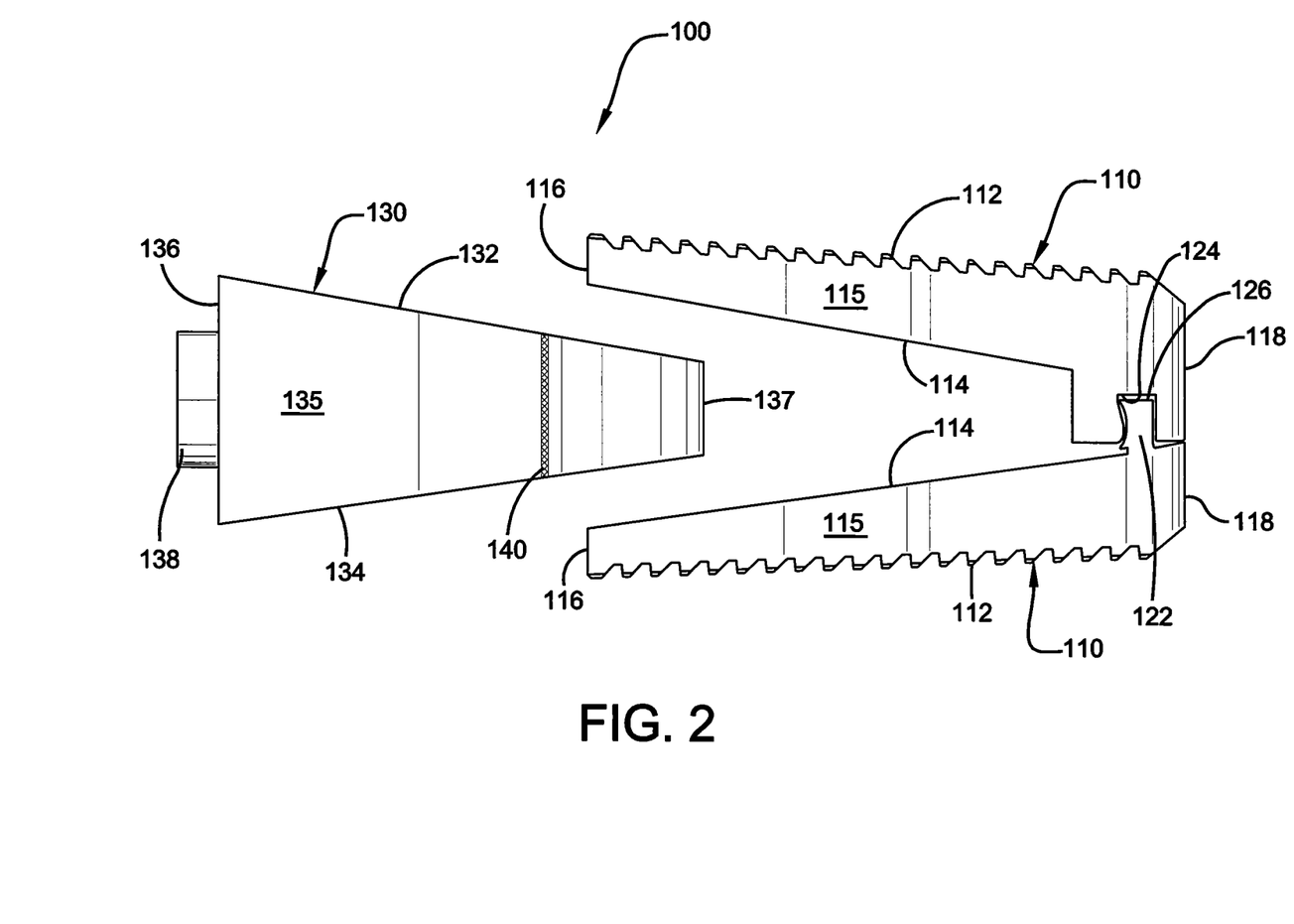
FIG. 2 illustrates a side elevational and exploded view of the vertebral implant of FIG. 1.

Posterior portions 118 preferably have a generally rounded nose profile, and a shorter height than anterior portions 116, such that the endplates 110 comprises a lordotic angle for aligning the spine of a patient. Further, endplates 110 are movably attached at their posterior ends 118 by a slip joint 120 or other suitable securing mechanism as is known in the art. More specifically, slip joint 120 is preferably a sliding dovetail joint and is comprised of a male portion 122 and a female portion 124 for receipt of said male portion 122, as shown in FIGS. 1 and 2. A water-soluble support material 126 may also be positioned around slip joint 120. Once the pair of endplates 110 is formed, support material 126 may be dissolved away, allowing the pair of endplates 110 to move independently from one another, but to still remain movably attached via the slip joint 120, such that the pair of endplates 110 allow for height expansion and lordotic angle change of implant 100.

Figure 4A:
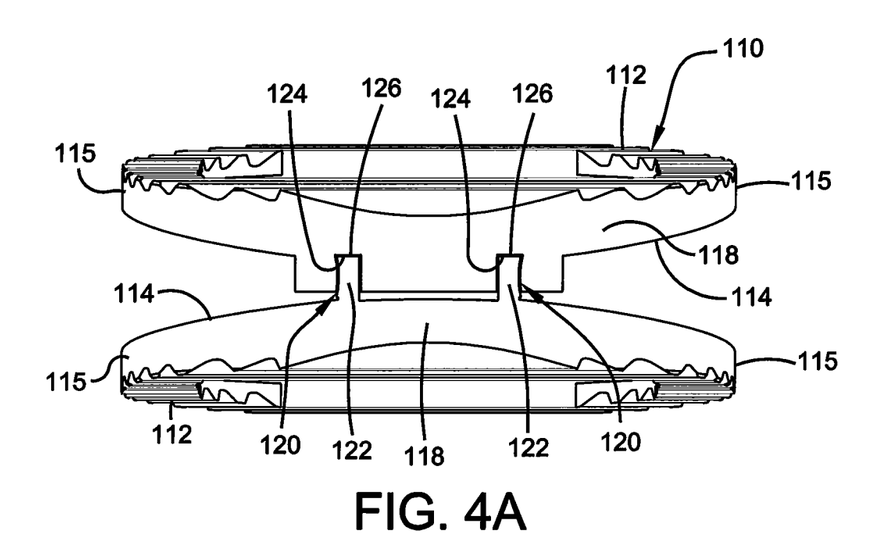
FIG. 4A illustrates an anterior elevational view of the end plates of the vertebral implant of FIG. 1.
Figure 4B:
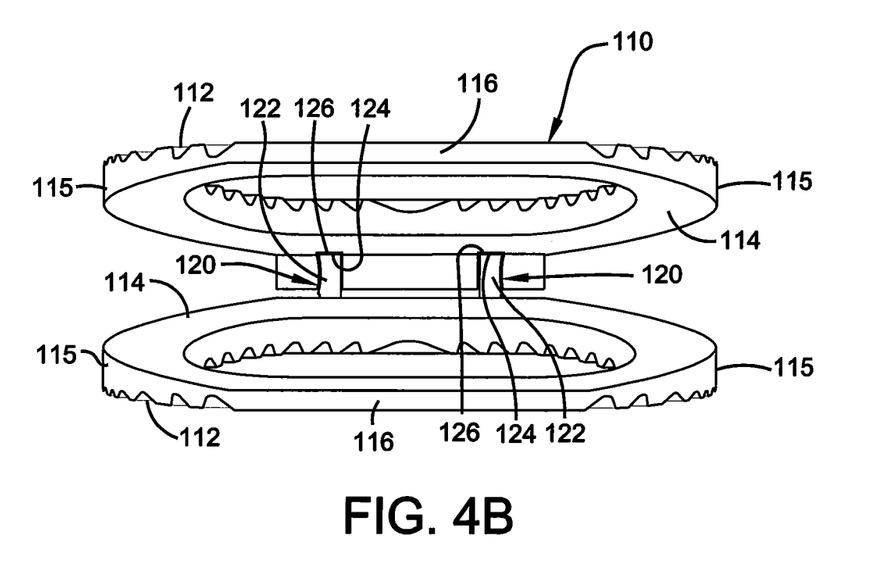
FIG. 4B illustrates a posterior elevational view of the end plates of the vertebral implant of FIG. 1.

Notwithstanding, one of ordinary skill in the art will appreciate that the shape and size of the endplates 110, as shown in FIGS. 1, 2 and 4A and B, are for illustrative purposes only and that many other shapes and sizes of endplates 110 are well within the scope of the present disclosure. Although dimensions of endplates 110 (i.e., length, width, and height) are important design parameters for good performance, endplates 110 may be any shape or size that ensures optimal performance during use.

Figure 3A:
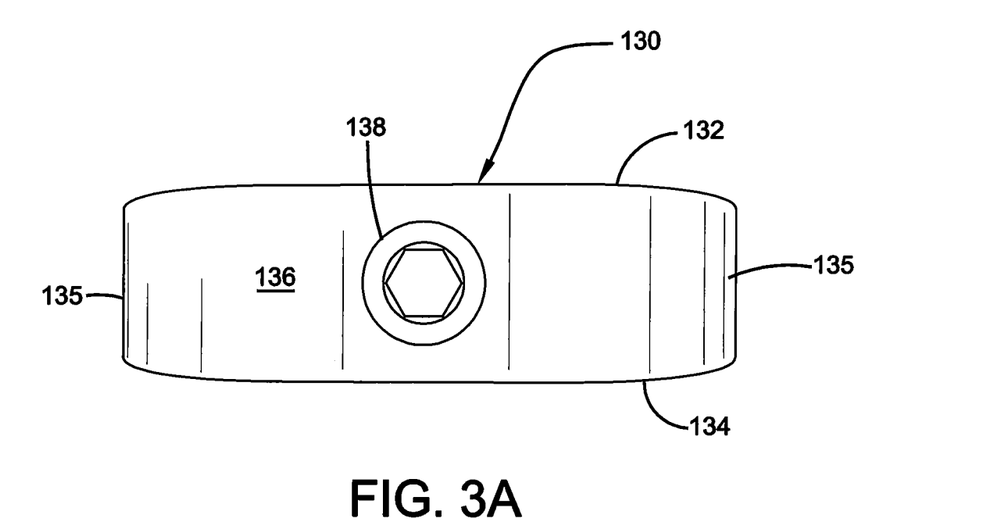
FIG. 3A illustrates an anterior elevational view of the wedge component of the vertebral implant of FIG. 1.

As best shown in FIGS. 1, 2 and 3A and B, wedge component 130 comprises a top surface 132, a bottom surface 134, opposing lateral sides 135, opposing anterior 136 and posterior portions 137, a bar lock 138 positioned on said anterior portion 136, and a continuous opening 139 therein extending from the top surface 132 to the bottom surface 134 of the wedge component 130 to, among other things, promote bone growth. Further, the lateral sides 135 may also comprise at least one vertical rod or other structure 140 containing structurally encoded data, as described more fully below.

Figure 3B:
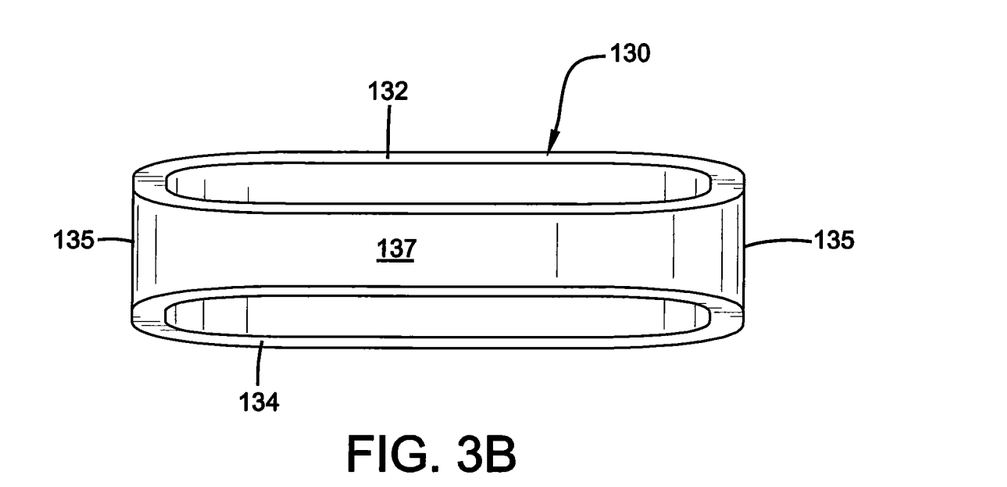
FIG. 3B illustrates a posterior elevational view of the wedge component of the vertebral implant of FIG. 1.

Typically, the height of wedge component 130 is greatest at its anterior portion 136 and tapers at an angle in the direction of the posterior portion 137 of wedge component 130. As mentioned above, wedge component 130 further comprises a rotatable bar lock 138 or other similar lock or protrusion which engages the endplates 110 to prevent the wedge component 130 from being removed from between the endplates 110 once installed in a patient. More specifically, bar lock 138 is positioned on the anterior portion 136 of wedge component 130, and preferably extends through anterior portion 136 and into continuous opening 139. Upon installation, an inserter tool (not shown) would engage the bar lock 138 to rotate the same such that a section of the bar lock 138 contacts an interior section of one or more of the endplates 110, thereby preventing the wedge component 130 from being removed from the endplates 110.

Notwithstanding the forgoing, one of ordinary skill in the art will appreciate that the shape and size of wedge component 130 as shown in FIGS. 1, 2 and 3A and B are for illustrative purposes only and many other shapes and sizes of wedge component 130 are well within the scope of the present disclosure. Although dimensions of wedge component 130 (i.e., length, width, and height) are important design parameters for good performance, wedge component 130 may be any shape or size that ensures optimal performance during use and is within the overall objective of the present invention. For example, wedge component 130 can be of varying heights and lordotic angles, and is inserted between endplates 110 to change the height of implant 100, as well as its lordotic angle. Specifically, the pair of endplates 110 would be implanted in a collapsed state in the disc space of a user (not shown), and then the wedge component 130 would be inserted between the endplates 110 to push apart the endplates 110 at their anterior ends 116 and to raise the posterior end 118 via the sliding dovetail joint 120, such that the height and lordotic angle of implant 100 is increased to the desired height and angle needed.

Typically, implant 100 of the present invention may be manufactured using additive manufacturing (AM) techniques, or using a combination of other molding or machining techniques (injection molding, machining, etc.) to produce the subject encoded implants. These additional techniques include, without limitation, material extrusion, vat photo polymerization, powder bed fusion, material jetting, binder jetting, sheet lamination and directed energy deposition. Endplates 110 are preferably manufactured from titanium, specifically Ti 6 Al 4 V-ELI, but can be manufactured from any other suitable material as is known in the art. Similarly, wedge component 130 is preferably manufactured from a polymer, specifically PEEK (polyetheretherketone), but can be manufactured from any other suitable material as is known in the art.

In a preferred embodiment, endplates 110 are manufactured (or grown) together as one integral component using additive manufacturing techniques. Further, as mentioned above, the endplates 110 comprise a slip joint 120 or other suitable joint as is known in the art. The slip joint 120 holds the endplates 110 removably in place at their posterior ends 118. Support material 126 may be added during the additive manufacturing process to lend support to the apertures in slip joint 120, and is positioned around the slip joint 120 during manufacturing of implant 100. Specifically, the support material 126 holds the endplates 110 in place as both components are formed. Support material 126 is preferably a water-soluble support material, but can be any suitable water-soluble material as is known in the art. Once formed, the support material 126 may be dissolved away, thereby allowing the two endplates 110 to move independently from one another, but to still remain movably attached via slip joint 120.

As referenced above, wedge component 130, or any other portion of implant 100, may further comprise structurally encoded data. By way of example, portions of implant 100 such as the surface or interior of endplates 110 or wedge component 130, may also comprise notches or other radiopaque inclusions that interrupt an otherwise uniform surface (or that have a varying density) and that can be encoded with information about the implant 100, its manufacturer, the patient, the facility or physician performing the procedure, etc. in accordance with the inventions disclosed in the incorporated references. The structurally encoded data may also take the form of the rods 140 of the lateral wall structure of the wedge component 130 shown in the FIGS., or the vertical rods 140 can be tantalum rods, that can be coded to match the encoded markers that may be pressed into the implant 100 in accordance with inventions disclosed in the incorporated references. Such encoding may be accomplished for instance through the use of eclipsing patterns of marks or notches in other planes within the wedge component 4, to reveal a pattern upon elucidation through reading illumination or through illumination-aided visual inspection or optical inspection, as described herein.

The displayed pattern may be used and stored as a unique symbol such as may be done in a fashion similar to bar codes, or other direct correspondence to a file of information such as through pattern recognition. The encoded pattern may further be associated with a database containing a plurality of records associated with a plurality of implantable devices 100 and a user interface comprising means for displaying information associated with the indicia based on the plurality of records. The encoded pattern may in turn be related to a unique numerical identifier corresponding to the associated manufacturer, serial number, installation data, patient, surgeon, or surgical procedure information that may be located in an external healthcare facility or other database.

The structurally encoded member 140 may be read via a system selected from the group consisting of visible light, UV light, x-ray, fluoroscopy, computed tomography, electromagnetic radiation, ultrasound, ultrasound, magnetic resonance imaging, positron emission tomography and neutron imaging. The information or data encoded onto or into the implants of the embodiments disclosed in the present invention may also be detected, decoded, read, transferred, stored, displayed, or processed according to such methods and devices disclosed in U.S. Pat. No. 8,233,967 or U.S. Patent Application Publication No. 2013/0053680, both of which are incorporated herein by reference.

The present invention thus permits the convenient, accurate and efficient reading of structurally encoded articles such as the implant 100 of the present invention. A typical embodiment of the structurally encoded implants 100 of the present invention may contain data that is not readily apparent to a viewer of the device structure. Further, encoding of the typical embodiments of the present invention is handled by physical means other than those accomplished through circuitry, electromagnetic or other, within the implant device itself or through a type of internal storage means such as magnetic storage means or the like. Such structurally encoded devices, as disclosed herein and described in relation to the typical and/or preferred embodiments of the present invention allow simplified production, maintenance, and/or operation costs for identification, storage, and/or retrieval of unique implant data while retaining a substantial amount of information with reduced probability for error.

The implant 100 of the present invention also enables better reporting, reviewing, inventorying and analyzing of implant devices 100 to reduce medical error by enabling healthcare professionals and others to rapidly and precisely identify an implant device 100 and obtain important information concerning the characteristics of the device, principally prior to installation. The present invention enhances analysis of implants on the market by providing a standard and clear way to document device use in electronic health records, clinical information systems, claim data sources, and registries.

It will also be appreciated that the present invention may be applied to similarly prepared articles such as articles that may benefit from structurally encoded structures as in the present invention. Such articles may include parts used in manufacturing, such as in the case of automobiles and parts therefor, firearms and parts therefor or jewelry and parts therefor. The present invention also includes methods of reading the structurally encoded articles, as well as an inventory management system for structurally encoded articles that includes reading the encoded data from the encoded articles and storing the acquired data, as described in the references cited herein.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implant comprising:
   a pair of endplates having a posterior surface, an anterior surface, and opposing sides, wherein the pair of endplates are movably attached to one another by a sliding dovetail joint located on the posterior surface of the implant, and further wherein a range of motion of the pair of endplates at the posterior surface is less than a second range of motion of the pair of endplates at the anterior surface;
   at least one structurally encoded member; and
   a wedge component positioned at least partially between said pair of endplates, wherein the positioning of the wedge component modifies the height and lordotic angle of the implant.

2. The implant of claim 1, wherein each of said pair of endplates move independently from one another and comprise an outboard surface, an inboard surface, and a continuous opening extending from said outboard surface to said inboard surface.

3. The implant of claim 2, wherein the outboard surface comprises a roughened surface topography.

4. The implant of claim 1, wherein said sliding dovetail joint comprises a male portion and a female portion.

5. The implant of claim 1, wherein the wedge component comprises a height, an anterior portion, a posterior portion and a rotatable bar lock, and further wherein the height of the wedge component is greatest at the anterior portion.

6. The implant of claim 5, wherein the rotatable bar lock secures the wedge component to at least one of said pair of endplates.

7. The implant of claim 1, wherein the pair of endplates are manufactured using additive manufacturing techniques.

8. The implant of claim 1, further comprising a support material positioned adjacent to the sliding dovetail joint.

9. The implant of claim 8, wherein the support material is water soluble.

10. An implant comprising:
a pair of endplates having a posterior surface, an anterior surface, and opposing sides, wherein the pair of endplates are movably attached to one another by a sliding dovetail joint located on the posterior surface of the implant, and further wherein a range of motion of the pair of endplates at the posterior surface is less than a second range of motion of the pair of endplates at the anterior surface;
a wedge component positioned at least partially between said pair of endplates; and
at least one structurally encoded member.

11. The implant of claim 10, wherein each of said pair of endplates comprising an outboard surface, an inboard surface, and a continuous opening extending from said outboard surface to said inboard surface.

12. The implant of claim 10, wherein said sliding dovetail joint comprises a male portion and a female portion.

13. The implant of claim 10, wherein said wedge component is comprised of a height, an anterior section, a posterior section, and a rotatable bar lock, and further wherein the height of the wedge component is greater at the anterior section than at the posterior section.

14. The implant of claim 10 further comprising a height and a lordotic angle, wherein the positioning of the wedge component between the pair of endplates modifies at least one of the height and the lordotic angle.

15. The implant of claim 10, wherein the at least one structurally encoded member is positioned on a sidewall of the wedge component.

16. The implant of claim 10, wherein the structurally encoded member is read via a system selected from the group consisting of visible light, UV light, x-ray, fluoroscopy, computed tomography, electromagnetic radiation, ultrasound, ultrasound, magnetic resonance imaging, positron emission tomography and neutron imaging.

17. An implant comprising:
a pair of endplates that move independently from one another and having a posterior surface, an anterior surface, and opposing sides, wherein each of the pair of endplates comprise an outboard surface, an inboard surface, and a continuous opening extending from the outboard surface to the inboard surface;
a wedge component comprised of a top surface, a bottom surface and a continuous opening that extends from said top surface to said bottom surface; and
a sliding dovetail joint that connects the pair of endplates together, wherein said sliding dovetail joint is located on the posterior surface of the implant, and further wherein a range of motion of the pair of endplates at the posterior surface is less than a second range of motion of the pair of endplates at the anterior surface.

18. The implant of claim 17, wherein the wedge component is positioned between the pair of endplates.

19. The implant of claim 17 further comprising a support material.

20. The implant of claim 19, wherein said support material is water soluble.

* * * * *